US012329903B2

(12) United States Patent
Kaczkowski

(10) Patent No.: US 12,329,903 B2
(45) Date of Patent: Jun. 17, 2025

(54) SYSTEM AND METHOD FOR A FLUID DISPERSAL CARTRIDGE

(71) Applicant: Hypnos Virtual, Inc, Little Rock, AR (US)

(72) Inventor: Michael Kaczkowski, Little Rock, AR (US)

(73) Assignee: Hypnos Virtual, Inc., Little Rock, AR (US)

( * ) Notice: Subject to any disclaimer, the term of this patent is extended or adjusted under 35 U.S.C. 154(b) by 25 days.

(21) Appl. No.: 17/689,517

(22) Filed: Mar. 8, 2022

(65) Prior Publication Data

US 2023/0264214 A1 Aug. 24, 2023

Related U.S. Application Data

(60) Provisional application No. 63/311,530, filed on Feb. 18, 2022.

(51) Int. Cl.

| | |
|---|---|
| ***A61M 15/06*** | (2006.01) |
| ***A61M 15/00*** | (2006.01) |
| ***B05B 7/24*** | (2006.01) |

(52) U.S. Cl.

CPC .......... *A61M 15/06* (2013.01); *A61M 15/002* (2014.02); *B05B 7/2489* (2013.01); *A61M 2205/8206* (2013.01)

(58) Field of Classification Search

CPC ................ A61M 15/06; A61M 15/002; A61M 2205/8206; B05B 7/2489

USPC ........................................ 239/124, 340, 369

See application file for complete search history.

(56) References Cited

U.S. PATENT DOCUMENTS

| | | | | |
|---|---|---|---|---|
| 2,205,559 | A * | 6/1940 | Heftler | F16N 7/34 239/340 |
| 4,595,127 | A * | 6/1986 | Stoody | B65D 83/20 239/113 |
| 7,407,118 | B2 | 8/2008 | Sevy | |
| 7,878,418 | B2 | 2/2011 | Sevy | |
| 8,047,813 | B2 | 11/2011 | Sevy | |
| D735,309 | S | 7/2015 | Sevy | |
| 9,415,130 | B2 | 8/2016 | Sevy | |
| 9,480,769 | B2 | 11/2016 | Sevy | |
| 9,895,464 | B2 | 2/2018 | Sevy | |
| 9,943,621 | B2 | 4/2018 | Sevy | |
| 10,245,345 | B2 | 4/2019 | Sevy | |
| 10,258,714 | B2 | 4/2019 | Sevy | |
| 10,507,258 | B2 | 12/2019 | Sevy | |
| 10,806,817 | B2 | 10/2020 | Sevy | |

(Continued)

*Primary Examiner* — Christopher S Kim

(74) *Attorney, Agent, or Firm* — EVAN LAW GROUP LLC

(57) ABSTRACT

A cartridge designed to dispense fluid via atomization is provided. The system generally comprises a cartridge, fluid, manifold, and air supply, wherein the air supply injects air through the manifold and into the cartridge through an air inlet of the cartridge. The air is manipulated by the cartridge in a way that creates a stream of fast-moving air above a fluid within the cartridge. This results in a zone of lower pressure above the fluid that results in the fluid to be suctioned into said stream of fast-moving air where it is atomized. The atomized fluid is then carried by the stream of fast-moving air out an atomization outlet where it is dispersed within the environment.

18 Claims, 10 Drawing Sheets

(56) References Cited

U.S. PATENT DOCUMENTS

| | | | |
|---|---|---|---|
| 2019/0290798 | A1 | 9/2019 | Sevy |
| 2020/0171195 | A1 | 6/2020 | Sevy |

* cited by examiner

SYSTEM AND METHOD FOR A FLUID DISPERSAL CARTRIDGE

CROSS REFERENCES

This application claims the benefit of U.S. Provisional Application No. 63/311,530, filed on Feb. 18, 2022, which application is incorporated herein by reference.

FIELD OF THE DISCLOSURE

The subject matter of the present disclosure refers generally to a system and method for a cartridge designed to dispense fluid via atomization/diffusion.

BACKGROUND

Plant essences, botanical fluids, and other plant distillates, commonly called "essential oils," are distilled fluids of plants, vegetables, nuts, seeds, roots, bark, flowers, etc. In some cases these distilled fluids can be made from non-organic substances as well but these will be included within the term "essence", "botanical fluid", "essential oil" or just "fluid" for sake of simplicity as well as "isolates" will also be included within these terms. These botanical fluids and essences typically have medicinal and/or therapeutic properties in addition to their valuable aromas that can be used in combination to create desirable fragrances. Unfortunately, the extraction of botanical fluids and essences from source plants is sometimes complicated, and comparatively expensive, based on the cost per unit volume of the botanical fluid and essence. As a result, colognes, perfumes, olfactory displays, and the like often use high rates of diluents with essences to reduce cost. They also may incorporate synthetic fluids, oils and artificial scents that may not replicate the comforting, familiar, and natural aroma of the natural essence. And most importantly, do not contain the beneficial medicinal and/or therapeutic properties the botanical fluids and essences possess due to their complex organic chemistry. Therefore, there has been interest in ways to efficiently disperse essences in a way that best keep their beneficial bio-chemical properties.

Evaporation rates or atomization rates of essences are often inadequate though, meaning that in order to provide a controllable, sustainable, and sufficient amount of said botanical fluids in the surrounding environment to achieve a desired effect, one must provide some sort of mechanism to increase the amount in the environment. Therefore, one of the most common methods of atomization, wicking diffusers, often prove inadequate since they possess no air movement mechanism. As a result, other forms of diffusion have become increasingly popular for dispensing botanicals throughout an environment. These methods of diffusion include ultrasonic diffusers, oil lamps, candle diffusers, and aroma heaters, which all work by heating a fluid so that a botanical is dispersed into the surrounding environment. Though these are all effective methods of diffusion, heat often destroys or at least changes the constitution of essences. Thus, these methods of diffusion have limitations.

Further, hypersonic diffusers/atomizers work by diffusing water particles into the surrounding environment, wherein said water particles then carry the botanical fluids into the surrounding environment. This results in the dilution of the botanical fluids in addition to increasing the humidity of the environment, which may not be a desired feature. To make matters worse, water, botanical fluids, and/or essences diffused by hypersonic diffusers often damage surrounding equipment, furniture, and objects within the environment. Moreover, the "spitting" of botanical fluids and/or essences into the surrounding environment by hypersonic diffusers results in comparatively large droplets of said botanical fluids and/or essences, which can not only be particularly devastating to finishes of furniture but also wastes a substantial fraction of the botanical fluids and/or essences, driving up the cost to the user of said hypersonic diffuser.

Accordingly, there is a need in the art for a system that distributes botanical fluids and essences into a surrounding environment more efficiently than current methods can achieve.

SUMMARY

A system and method for a cartridge used to distribute a fluid via cold-air atomization is provided. In one aspect, the system distributes fluid into its surrounding environment via a jet of air. In another aspect, the system holds a fluid designed in a position such that it is pulled into the atmosphere by a jet of air. Generally, air from an air supply enters an air inlet of a cartridge, wherein it is manipulated by the cartridge in a way that creates a stream of fast-moving air above a fluid within the cartridge, which causes the fluid within the to be suctioned into said stream of fast-moving air where it is atomized. The atomized fluid is then carried by the stream of fast-moving air out the atomization outlet where it is dispersed within the environment. Therefore, the system of the present embodiment atomizes fluid into the surrounding environment without the need of heat or a carrier fluid such as water.

The system generally comprises a fluid, cartridge, manifold, and air supply, wherein the air supply injects air through the manifold and/or cartridge in a way that causes the fluid to atomize. The cartridge comprises a hard casing having an air inlet, atomization outlet, fluid reservoir, vacuum channel, and air duct. The manifold comprises at least one attachment point for removably securing the cartridge thereto. An air outlet of the manifold is configured to align with the air inlet of the cartridge. The air supply may secure to the manifold in a way such that it may provide air to the cartridge through the manifold. As air is pushed through the air duct of the cartridge by the air supply, a choke point within the air duct causes the air to become of a stream of fast-moving air. Because the choke point is located directly in front of the point in which the air duct meets the vacuum channel, a zone of reduced pressure is created above the vacuum channel, resulting in the atomized.

The foregoing summary has outlined some features of the system and method of the present disclosure so that those skilled in the pertinent art may better understand the detailed description that follows. Additional features that form the subject of the claims will be described hereinafter. Those skilled in the pertinent art should appreciate that they can readily utilize these features for designing or modifying other structures for carrying out the same purpose of the system and method disclosed herein. Those skilled in the pertinent art should also realize that such equivalent designs or modifications do not depart from the scope of the system and method of the present disclosure.

DESCRIPTION OF THE DRAWINGS

These and other features, aspects, and advantages of the present disclosure will become better understood with regard to the following description, appended claims, and accompanying drawings where:

DETAILED DESCRIPTION

In the Summary above and in this Detailed Description, and the claims below, and in the accompanying drawings, reference is made to particular features, including method steps, of the invention. It is to be understood that the disclosure of the invention in this specification includes all possible combinations of such particular features. For instance, where a particular feature is disclosed in the context of a particular aspect or embodiment of the invention, or a particular claim, that feature can also be used, to the extent possible, in combination with/or in the context of other particular aspects of the embodiments of the invention, and in the invention generally.

The term “comprises” and grammatical equivalents thereof are used herein to mean that other components, steps, etc. are optionally present. For instance, a system “comprising” components A, B, and C can contain only components A, B, and C, or can contain not only components A, B, and C, but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

Figure 1:
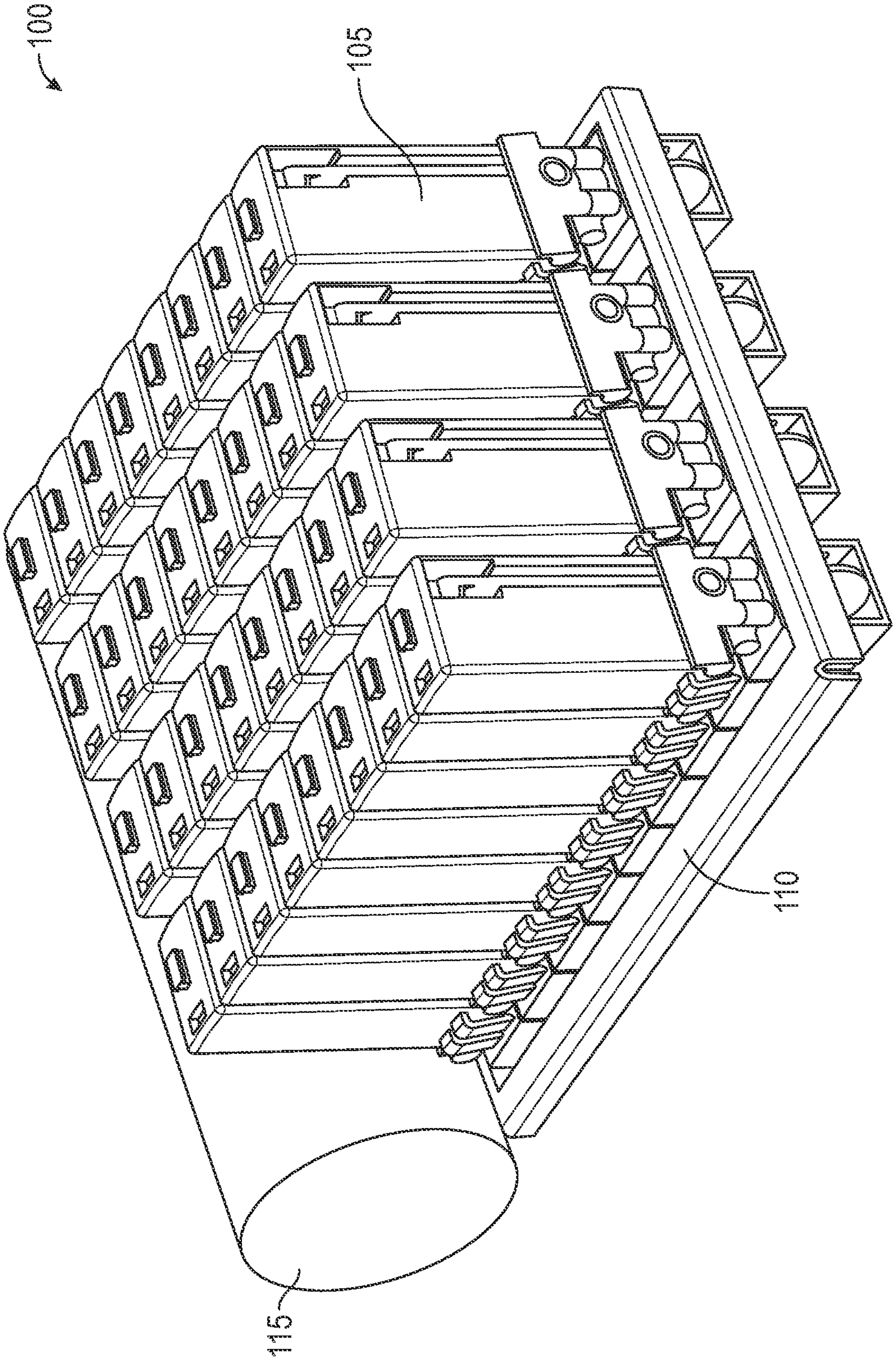
FIG. 1 is a perspective view of a system embodying features consistent with the principles of the present disclosure.
Figure 2:
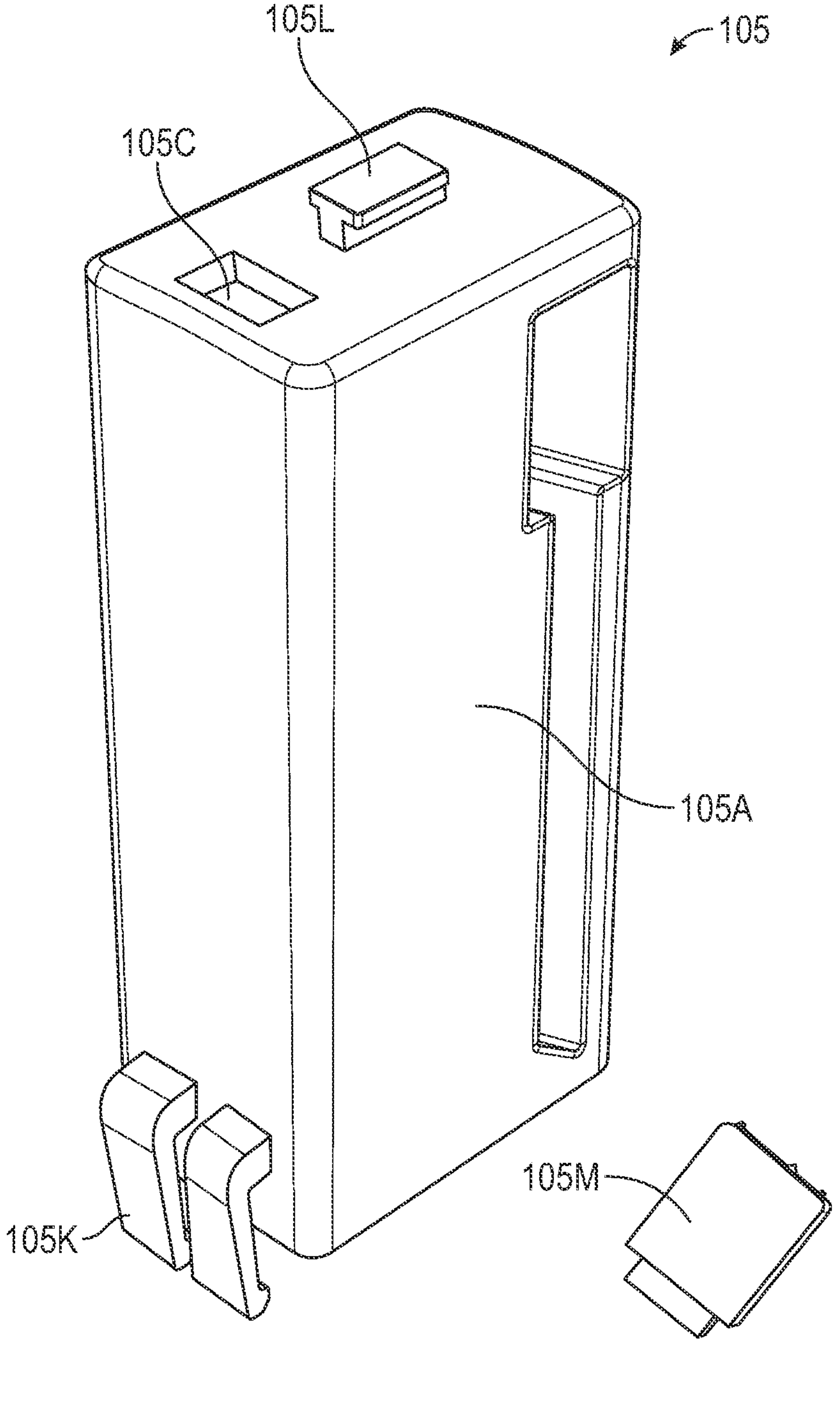
FIG. 2 is a perspective view of a cartridge embodying features consistent with the principles of the present disclosure.
Figure 3:
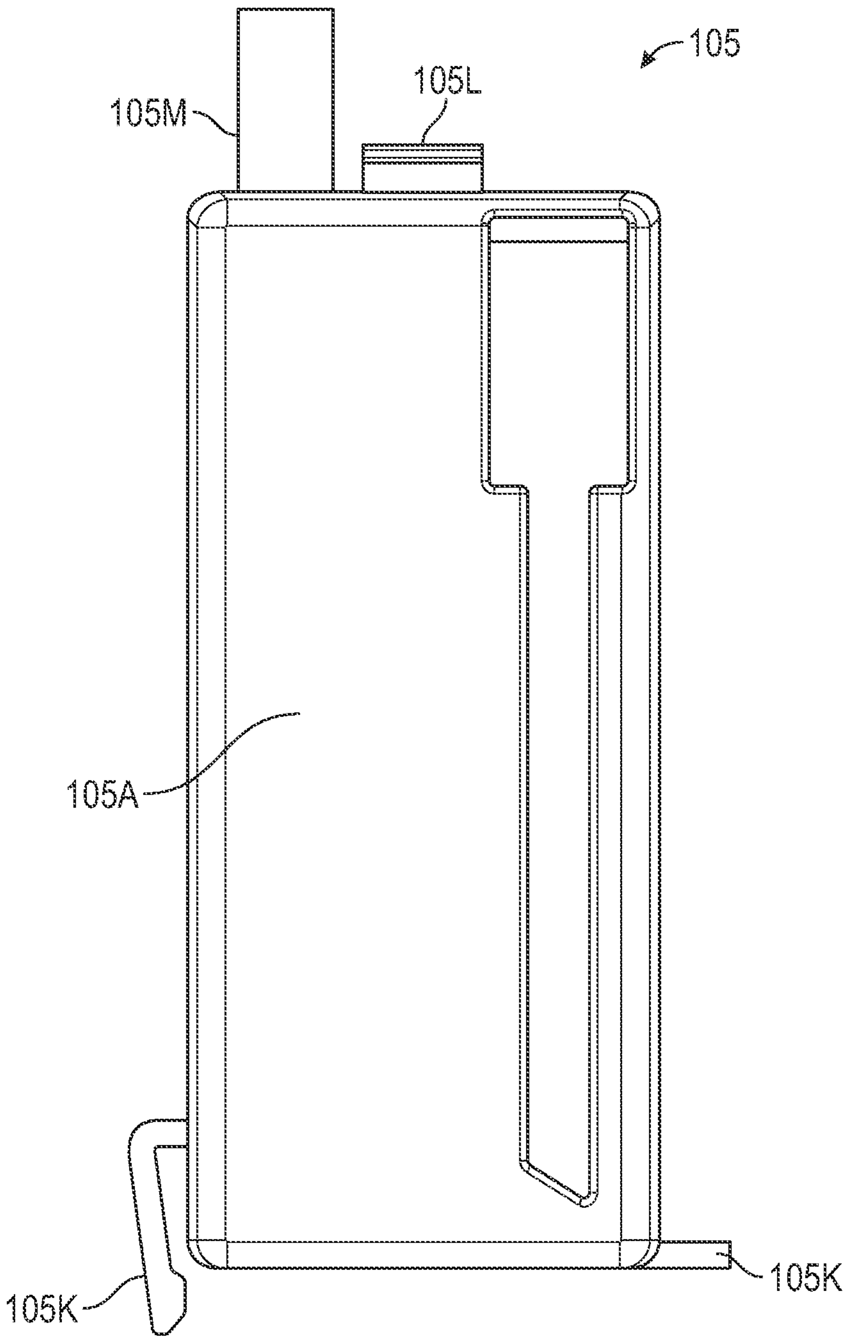
FIG. 3 is a front view of a cartridge embodying features consistent with the principles of the present disclosure.
Figure 4:
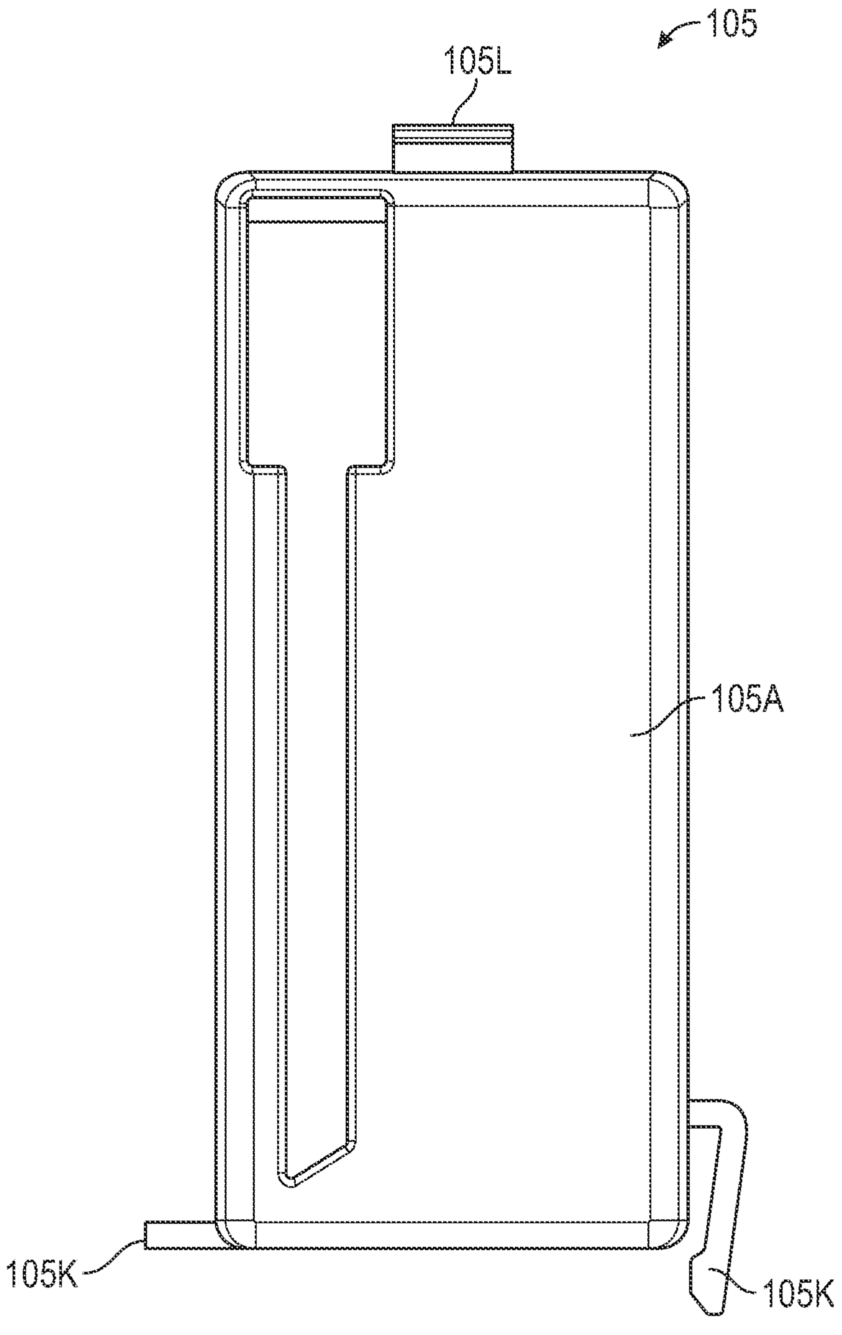
FIG. 4 is a back view of a cartridge embodying features consistent with the principles of the present disclosure.
Figure 5:
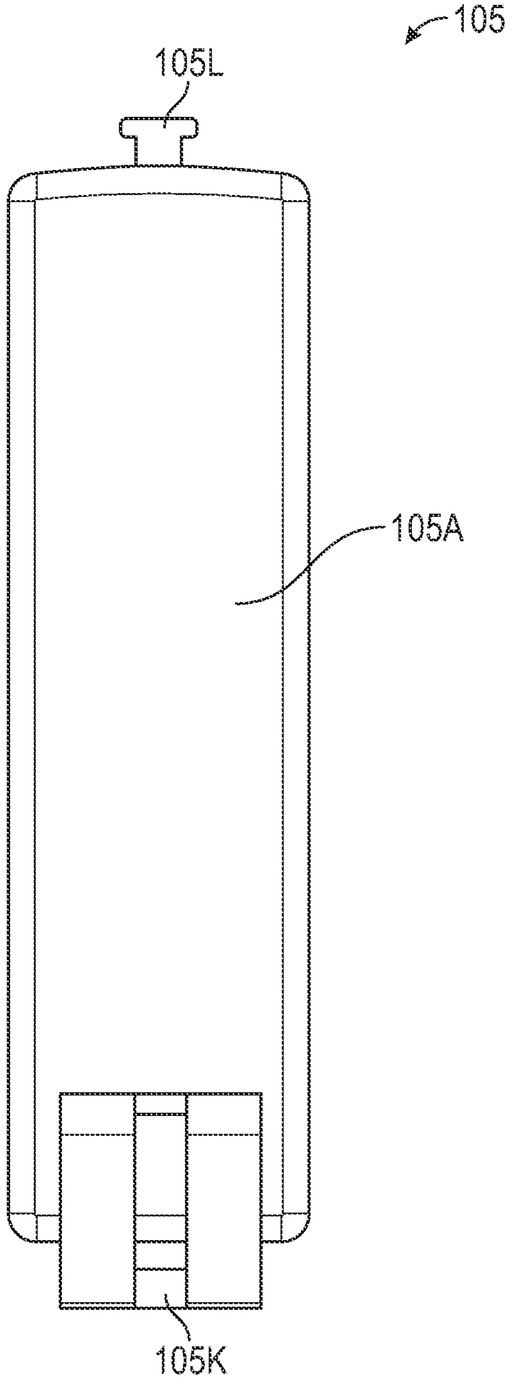
FIG. 5 is a left-side view of a cartridge embodying features consistent with the principles of the present disclosure.
Figure 6:
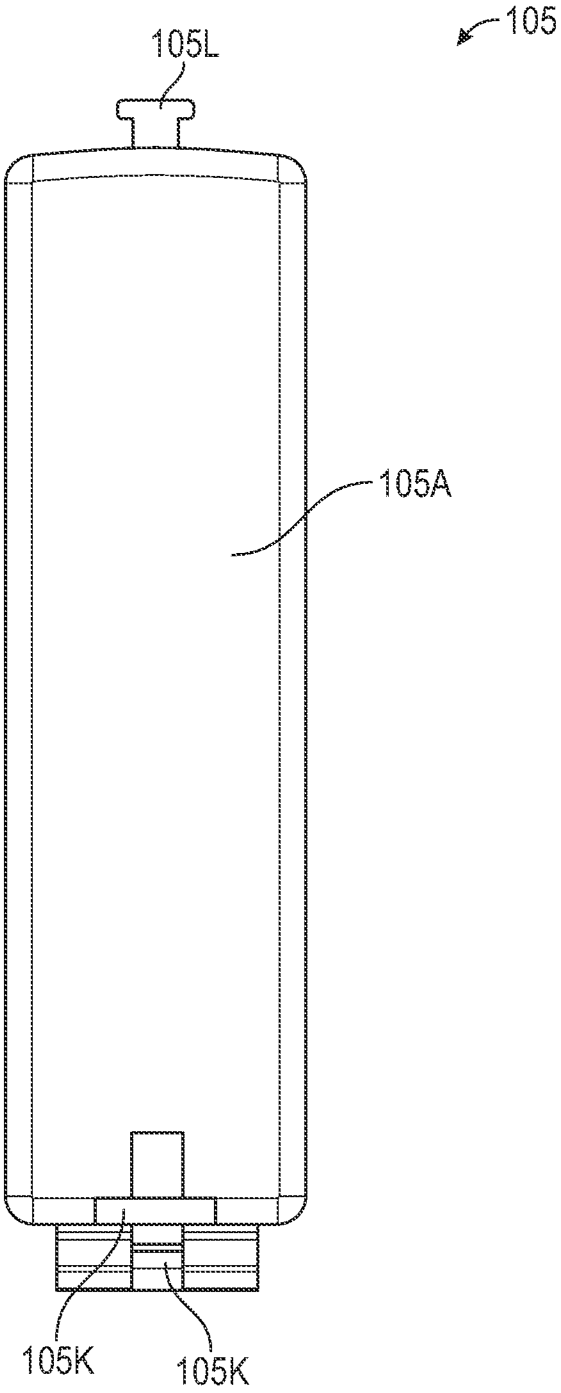
FIG. 6 is a right-side view of a cartridge embodying features consistent with the principles of the present disclosure.
Figure 7:
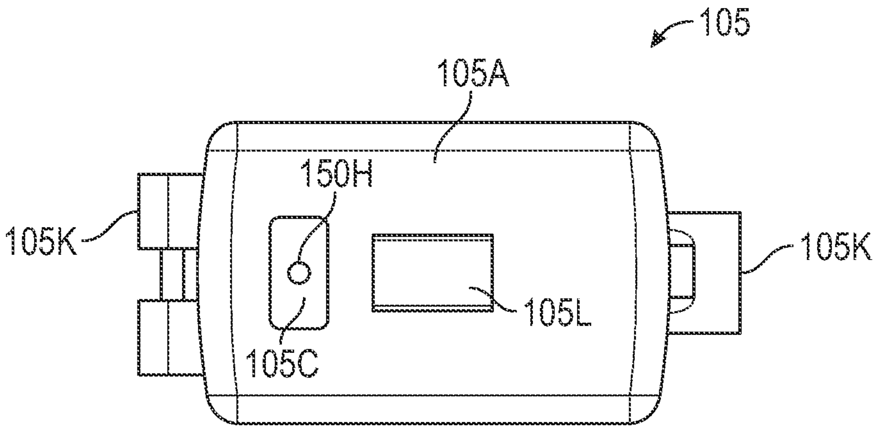
FIG. 7 is a top view of a cartridge embodying features consistent with the principles of the present disclosure.
Figure 8:
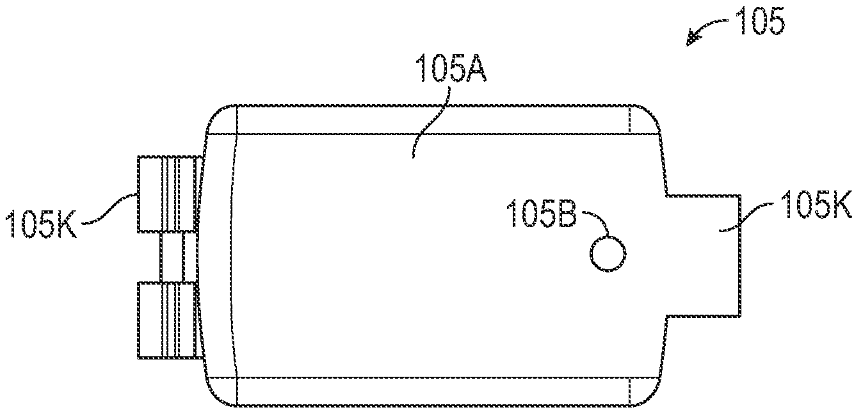
FIG. 8 is a bottom view of a cartridge embodying features consistent with the principles of the present disclosure.
Figure 9:
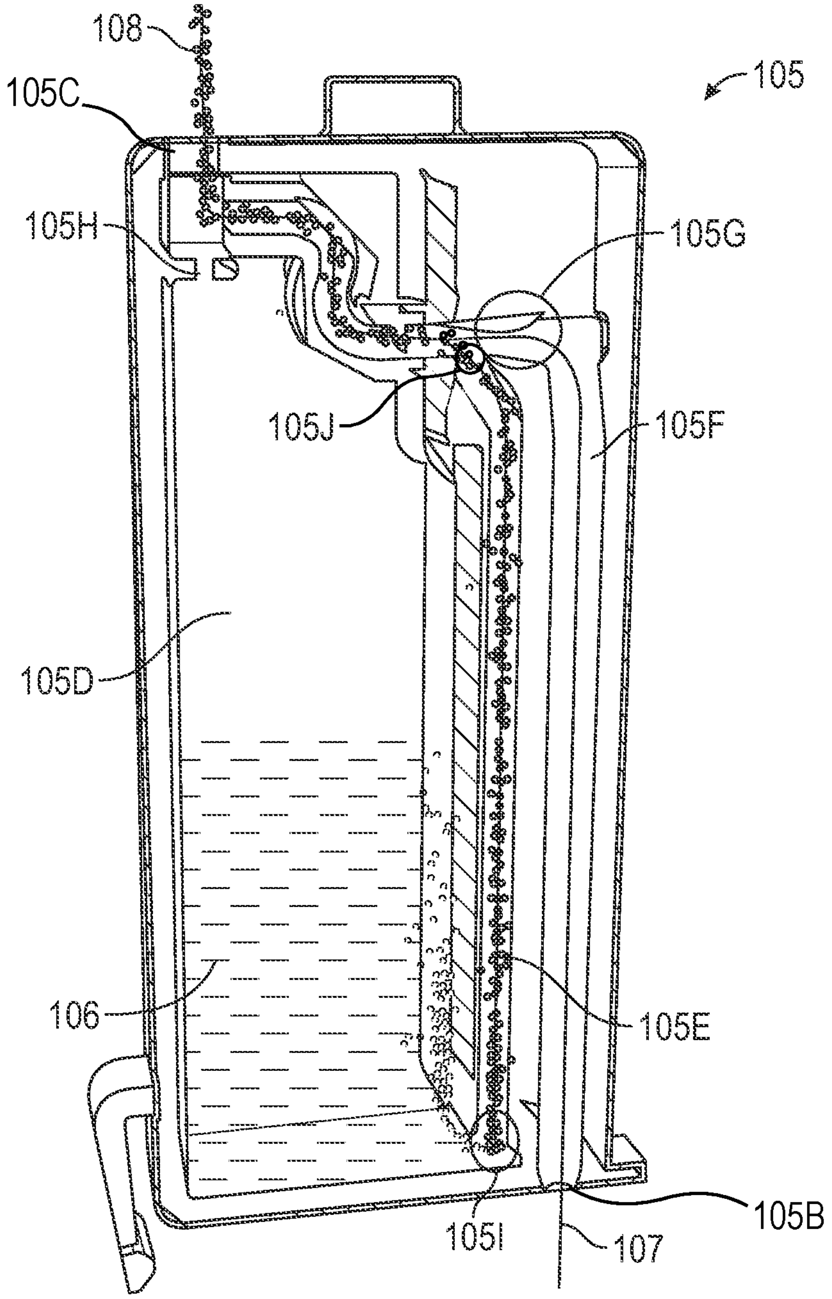
FIG. 9 illustrates how fluid and air flows through a cartridge embodying features consistent with the principles of the present disclosure.
Figure 10:
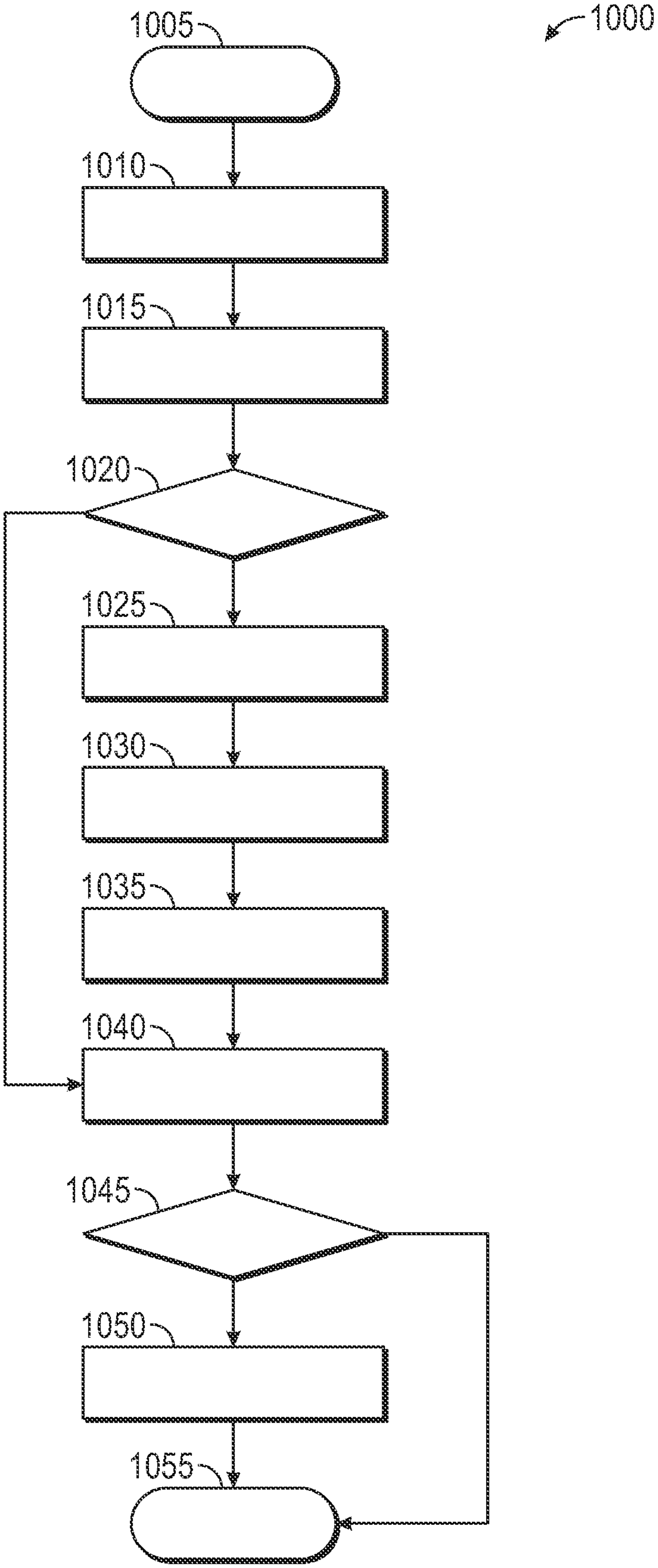
FIG. 10 is a flow chart illustrating certain method steps of a method embodying features consistent with the principles of the present disclosure.
Figure 11:
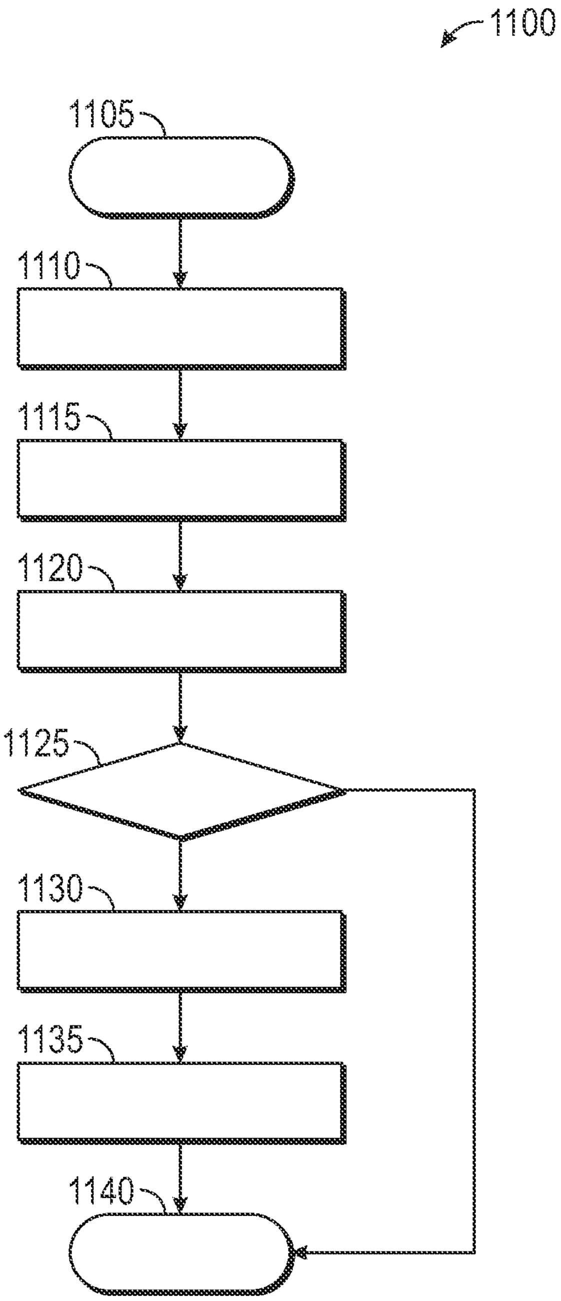
FIG. 11 is a flow chart illustrating certain method steps of a method embodying features consistent with the principles of the present disclosure.

FIGS. 1-11 illustrate embodiments of a system 100 configured to atomize a fluid 106 into an environment using air 107. FIG. 1 illustrates a perspective view of a system 100 designed to distribute a fluid 106 into a surrounding environment. FIG. 2 illustrates a perspective view of a cartridge 105 designed to distribute a fluid 106 into a surrounding environment. FIG. 3 illustrates a front view of a cartridge 105 designed to distribute a fluid 106 into a surrounding environment. FIG. 4 illustrates a back view of a cartridge 105 designed to distribute a fluid 106 into a surrounding environment. FIG. 5 illustrates a left-side view of a cartridge 105 designed to distribute a fluid 106 into a surrounding environment. FIG. 6 illustrates a right-side view of a cartridge 105 designed to distribute a fluid 106 into a surrounding environment. FIG. 7 illustrates a top view of a cartridge 105 designed to distribute a fluid 106 into a surrounding environment. FIG. 8 illustrates a bottom view of a cartridge 105 designed to distribute a fluid 106 into a surrounding environment. FIG. 9 illustrates the manner in which the cartridge 105 distributes fluid 106 into a surrounding environment. FIGS. 10 and 11 illustrate methods that may be carried out by a user using the cartridge 105. It is understood that the various method steps associated with the methods of the present disclosure may be carried out as operations by the system 100 depicted in FIGS. 1-9.

The system 100 generally comprises a fluid 106, cartridge 105, and air supply 115, wherein the air supply 115 injects air 107 through the cartridge 105 in a way that causes the fluid 106 to atomize. In one preferred embodiment, as illustrated in FIG. 1, the cartridge 105 is removably secured to a manifold 110 of the air supply 115 in a way that allows a user to remove a first cartridge 105 from the manifold 110 and secure a second cartridge 105 in its place, permitting a user to quickly replace cartridges 105 should the need arise. For instance, should a first cartridge 105 run out of fluid 106, the user may obtain a second cartridge 105 containing a desired fluid 106, remove the first cartridge 105 from the manifold 110, and secure the second cartridge 105 thereto. For instance, should the user desire a different fluid 106 to be atomized/nebulized/sprayed into the surrounding environment than that of the first cartridge 105, the user may swap the first cartridge 105 having a first fluid 106 with a second cartridge 105 having a second fluid 106.

As illustrated in FIGS. 1-9, the cartridge 105 comprises a hard casing 105A having an air inlet 105B and an atomization outlet 105C. In a preferred embodiment, the cartridge 105 is made of hard plastic, glass, enamel, or any combination thereof. However, other materials suitable for making a hard casing 105A may be used without departing from the inventive subject matter described herein. As illustrated in FIG. 9, a fluid reservoir 105D within the hard casing 105A is configured to hold the fluid 106 therein, and a vacuum channel 105E connected to said fluid reservoir 105D at a bottom connection point 1051 and an air duct 105F at a top connection point 1051 allows a portion of the fluid 106 to encounter the stream of fast-moving air 107. In a preferred embodiment, the air duct 105F moves air 107 having an initial velocity from the base end of the cartridge 105 towards a choke point 105G of the air duct 105F located towards the top end of the cartridge 105. The choke point 105G of the air duct 105F is a point in which the air duct 105F narrows, resulting in a lower cross-sectional area of the air duct 105F.

Additionally, in some preferred embodiments, as illustrated in FIG. 9, the air duct 105F is configured to expand past the choke point 105G and top connection point 1051 until it reaches the atomization outlet 105C and/or the outlet vent 105M, which causes the stream of fast-moving air 107 to be directed towards the environment. However, in other preferred embodiments, the air duct 105F may not extend past the choke point 105G and top connection point 1051 but instead opens up into the fluid reservoir 105D, allowing for atomized fluid to both collect within the fluid reservoir 105D and move out of the atomization outlet 105C and/or the outlet vent 105M. Because the choke point 105G is positioned directly upstream of the top connection point 105J, as illustrated in FIG. 9, the resulting Venturi effect causes the constricted air 107 to speed up as it reaches the top connection point 105J, resulting in a drop in pressure over said vacuum channel 105E. This drop in pressure causes the fluid 106 within the vacuum channel 105E to be suctioned into the stream of fast-moving air 107 at the top connection point 105J, where it is atomized and moved by the stream of fast-moving air 107 towards the atomization outlet 105C.

In some preferred embodiments, the hard casing 105A may further comprise an attachment element 105K, knob 105L, and outlet vent 105M, wherein the attachment element 105K and knob 105L are configured to used in conjunction with a manifold 110 while the outlet vent 105M works in conjunction with the atomization outlet 105C. The manifold 110 is configured in a way such that the air supply 115 attaches thereto so that the air supply 115 may supply air 107 to one or more cartridges 105 through said manifold 110. As illustrated in FIG. 1, a single manifold 110 may be used by an air supply 115 to provide air 107 to a single cartridge 105 or a plurality of cartridges 105 at once. A cartridge 105 may be secured to the manifold 110 using the attachment element 105K, and the knob 105L may be used to assist a user when removing a cartridge 105 from the manifold 110. In a preferred embodiment, the attachment element 105K is a locking tab and foot tab, as illustrated in FIGS. 1-9, which secure the base end of the cartridge 105 to the manifold 110. In a preferred embodiment, an air outlet of the manifold 110 is aligned with the air inlet 105B of the cartridge 105 such that air 107 is supplied to the cartridge 105 from the air supply 115 and through said manifold 110 when the base end of the cartridge 105 is secured to said manifold 110. The knob 105L is preferably located on the top end of the hard casing 105A, as illustrated in FIGS. 1-9, in a way that assists a user to grip the cartridge 105 when removing it from the manifold 110. This is necessary in instances when a cartridge 105 of a plurality of cartridges 105 secured to a manifold 110 is difficult to grip due to said cartridge's 105 location within said plurality of cartridges 105, as illustrated in FIG. 1.

As illustrated in FIGS. 2 and 3, an outlet vent 105M may be configured to secure within the atomization outlet 105C, changing the height and/or angle at which a fluid is diffused into a surrounding environment. The length and/or angle of the outlet vent 105M may vary based on the fluid 106 being dispersed by the cartridge 105. For instance, a fluid 106 that is more easily atomized and diffused into the surrounding environment may have an outlet vent 105M having a shorter length, wherein the shorter length only slightly increases the height in which the atomized fluid 108 is distributed. For instance, a fluid 106 that is less easily atomized and diffused into the surrounding environment may have an outlet vent 105M having a longer length, wherein the longer length greatly increases the height in which the atomized fluid 108 is distributed. Some cartridges 105 may not need an outlet vent 105M if the fluid 106 is exceptionally easy to diffuse into a surrounding environment. In some preferred embodiments of the cartridge 105, the outlet vent 105M may be incorporated into the hard casing 105A of the cartridge 105, moving the location of the atomization outlet 105C to the top of said outlet vent 105M.

The air supply 115 is configured to provide air 107 to the cartridge 105 so that the fluid 106 therein may be atomized and dispersed into the environment. Types of air supplies 115 that may be used by the system 100 include, but are not limited to, an air pump, air compressor, compressed air canister, or any combination thereof. In a preferred embodiment, an air pump is used to push air 107 through a cartridge 105 and/or manifold 110. In some preferred embodiments, the air pump may be secured to the manifold and/or cartridge via tubing. But in a preferred embodiment, the air pump may be incorporated into the manifold and/or cartridge that eliminates the need for tubing, creating a system with less parts that may be less prone to failure or necessitate cleaning less frequently. Additionally, filters of the air pump may be used to prevent the buildup of particulates in the manifold and/or cartridge, further eliminating the need for frequent cleaning. Types of air pumps that may be used by the system 100 include, but are not limited to, reciprocating pumps and rotary vane pumps. A switch of the pump may allow a user to activate the pump. In some preferred embodiments, one or more secondary switches may allow a user to control output of the pump, causing the pump to increase or decrease the flow of air 107 moving through the cartridge 105 and/or manifold 110.

The system 100 may comprise a power supply. The power supply may be any source of power that provides the air supply 115 with electricity. In one preferred embodiment, the system 100 may comprise of multiple power supplies that may provide power to the system 100 in different circumstances. For instance, the system 100 may be directly plugged into a stationary power outlet, which may provide power to the system 100 so long as it remains within a certain distance of said stationary power supply. However, the system 100 may also be connected to a mobile power supply, such as a battery, so that the system 100 may receive power even when the system 100 is not connected to a stationary power outlet. In this way, the system 100 may always receive power so that a user may atomize a fluid 106 regardless of the location.

The fluid 106 contained within the cartridge 105 is preferably a natural, concentrated, liquid aromatic or medicinal fluid with or without aroma, such as cannabidiol, essences, botanical fluids, essential oils, and terpenes. The fluid 106 may be injected into the fluid reservoir 105D via a reservoir hole 105H that may be accessed via the atomization outlet 105C, as illustrated in FIG. 9. Additionally, the reservoir hole 105H allows atomized fluid 108 that collects within the air duct 105F and around atomization outlet 105C to flow back into reservoir in way such that it does not block the air duct 105F. Therefore, in some preferred embodiments, the cartridge 105 may be refilled by the user once the fluid 106 within the reservoir is spent, and the cartridge 105 is self-cleaning in that air 107 moving through the cartridge 105 prevents debris from entering the atomization outlet 105C while recondensed atomized fluid 108 has at least one path that allows it to flow back to the fluid reservoir 105D. As such, a single cartridge 105 may be used to atomize a plurality of fluid 106*s* and/or mixture of fluid 106*s* without departing from the inventive subject matter herein.

FIG. 10 provides a flow chart illustrating certain, preferred method steps that may be used to carry out the method of swapping cartridges 105 to obtain the desired fluid 106 and then operating the system 100 to atomize the desired fluid 106. Step 1005 indicates the beginning of the method. During step 1010, the user may acquire a system 100 comprising a first cartridge 105, manifold 110, and air supply 115. During step 1015, the user may perform a query to determine if the first fluid 106 within the first cartridge 105 is the desired fluid 106. Based on the results of the query, the user may take an action during step 1020. If the user determines that the first fluid 106 within the first cartridge 105 is the desired fluid 106, the user may proceed to step 1040. If the user determines that the first fluid 106 is not the desired fluid 106, the user may obtain a second cartridge 105 having a second fluid 106 therein during step 1025, wherein the second fluid 106 is the desired fluid 106.

Once the user has acquired the second cartridge 105, the user may remove the first cartridge 105 from the manifold 110 during step 1030. In a preferred embodiment, the user must manipulate an attachment element 105K and knob 105L to remove the first cartridge 105 form the manifold 110. The user may then attach the second cartridge 105 to the manifold 110 in place of the first cartridge 105 during step 1035. The user may then perform a query to determine whether to turn on the air supply 115 during step 1040, wherein turning on the air supply 115 will cause the system 100 to atomize the desired fluid 106. Based on the results of the query, the user may perform an action during step 1045. If the user determines they do not want to atomize the desired fluid 106, the user may proceed to terminate method step 1055. If the user determines that they would like to atomize the desired fluid 106, the user may engage a switch of the air supply 115 that will cause said air supply 115 to draw power from the power supply and push air 107 through the cartridge 105 during step 1050, resulting in the desired fluid 106 becoming an atomized fluid 108. Once the air supply 115 has been turned on and the desired fluid 106 has become an atomized fluid 108, the method may proceed to terminate step 1055.

FIG. 11 provides a flow chart illustrating certain, preferred method steps that may be used to carry out the method of refilling spent cartridges 105 with a desired fluid 106. Step 1105 indicates the beginning of the method. During step 1110, the user may acquire a system 100 comprising a first cartridge 105, manifold 110, and air supply 115. During step 1115, the user may remove the cartridge 105 from the manifold 110 and may subsequently perform a query to to determine if there is a workable amount of desired fluid 106 within said cartridge 105 during step 1120. A workable amount of desired fluid 106 may be defined as the minimum amount of fluid 106 within a cartridge 105 that can be used by the system 100 to create an atomized fluid 108 at a desired rate. Based on the results of the query, the user may perform an action during step 1125. If the user determines that a workable amount of desired fluid 106 is contained within the fluid reservoir 105D of the cartridge 105, the user may proceed to terminate method step 1140. If the user determines that there is not a workable amount of desired fluid 106 within the fluid reservoir 105D, the user may obtain a quantity of desired fluid 106 during step 1130. The user may then add said quantity of desired fluid 106 to said cartridge 105 via the reservoir hole 105H and the atomization outlet 105C until a workable amount of desired fluid 106 is contained within the cartridge 105 during step 1135. Once the user has filled the cartridge 105 with a workable amount of desired fluid 106, the method may proceed to terminate method step 1140.

The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For instance, the implementations described above can be directed to various combinations and subcombinations of the disclosed features and/or combinations and subcombinations of several further features disclosed above. In addition, the logic flow depicted in the accompanying figures and/or described herein do not necessarily require the particular order shown, or sequential order, to achieve desirable results. It will be readily understood to those skilled in the art that various other changes in the details, materials, and arrangements of the parts and method stages which have been described and illustrated in order to explain the nature of this inventive subject matter can be made without departing from the principles and scope of the inventive subject matter.

What is claimed is:

1. A system configured to atomize/nebulize/spray a fluid with a stream of air under a Venturi effect comprising, a casing, wherein said casing comprises a fluid reservoir, a vacuum channel, and an air duct therein, wherein said fluid reservoir contains said fluid that is atomized within said casing, wherein said fluid reservoir intersects said vacuum channel at a bottom connection point of said vacuum channel, wherein said air duct has a first end at an air inlet and a second end at an atomization outlet, wherein said air duct intersects said vacuum channel at a top connection point of said vacuum channel, wherein said air inlet of said casing is configured to receive said stream of air at a base end of said casing, wherein said stream of air is pushed through said air duct and is accelerated at a choke point of said air duct and at said top connection point, wherein said choke point has a cross-sectional area that is smaller than a cross-sectional area of said air duct, wherein said fluid is suctioned under the Venturi effect from said vacuum channel and into said stream of air to atomizing said fluid, and wherein a reservoir hole connects said fluid reservoir with said air duct at a point between said top connection point and said atomization outlet.

2. The system of claim 1, wherein said stream of air causes said fluid to become an atomized fluid.

3. The system of claim 2, wherein said stream of air and said atomized fluid move to said atomization outlet configured to eject said stream of air and said atomized fluid.

4. The system of claim 3, further comprising an attachment element secured to the base end of said casing.

5. The system of claim 4, wherein:

said attachment element is configured to removably attach said casing to a manifold, an air outlet of said manifold aligns with said air inlet of said casing, an air supply is connected to said manifold and supplies said manifold with said air, and said air is transferred from said manifold to said casing via said air outlet of said manifold and said air inlet of said casing.

6. A system configured to atomize/nebulize/spray a fluid with a stream of air under a Venturi effect comprising:

a casing having a fluid reservoir, a vacuum channel, and an air duct therein, wherein the fluid reservoir contains the fluid, the fluid reservoir intersects the vacuum channel at a bottom connection point of the vacuum channel, the air duct intersects the vacuum channel at a top connection point of the vacuum channel, an air inlet of the air duct is configured to receive air at a base end of the casing, the air forms a first air stream which flows through the air duct and is converted into a second air stream at a narrowing of the air duct, the second air stream having a speed greater than the first air stream, and the narrowing of the air duct is located between the base end of the casing and the top connection point, to suction the fluid from the vacuum channel and into the second air stream under the Venturi effect, to atomizing the fluid, and the second air stream and the atomized fluid move to an atomization outlet configured to eject the second air stream containing the atomized fluid.

7. The system of claim 6, further comprising a knob located on a top end of the casing.

8. The system of claim 6, further comprising:

a manifold, having an air outlet, an air supply, connected to the manifold, wherein the manifold is configured to receive the air from the air supply, and the manifold is configured to deliver the air to the air inlet from the air outlet of the manifold.

9. The system of claim 8, wherein the air supply is at least one of an air pump and a compressed air canister.

10. A system configured to atomize fluid into an environment, comprising:

a manifold, a plurality of the systems of claim 6, with each system being a cartridge attached to the manifold, and an air supply, connected to the manifold, wherein the manifold is configured to receive the air from the air supply, and the manifold is configured to deliver the air to the air inlet of each of the cartridges.

11. The system of claim 10, wherein the air supply is at least one of an air pump and a compressed air canister.

12. A system configured to atomize/nebulize/spray a fluid with a stream of air under a Venturi effect comprising:

a casing having a fluid reservoir, a vacuum channel, and an air duct therein, wherein the fluid reservoir intersects the vacuum channel at a bottom connection point of the vacuum channel, the air duct intersects the vacuum channel at a top connection point of the vacuum channel, an air inlet of the air duct is at a base end of the casing, a narrowing of the air duct is located between the base end of the casing and the top connection point, an air outlet of the air duct is at a top end of the casing the system is configured such that when the fluid is present in the fluid reservoir and when the air forms a first air stream which flows through the air duct and is converted into a second air stream at the narrowing of the air duct, the second air stream has a speed greater than the first air stream, and the fluid is suctioned from the vacuum channel and into the second air stream under the Venturi effect, atomizing the fluid, and the air outlet is an atomization outlet.

13. The system of claim 12, further comprising a fluid connection between the air duct and the fluid reservoir, wherein the fluid connection intersects the air duct between the air outlet and the top connection.

14. The system of claim 13, further comprising a knob located on a top end of the casing.

15. The system of claim 13, further comprising:

a manifold, having an air outlet, an air supply, connected to the manifold, wherein the manifold is configured to receive the air from the air supply, and the manifold is configured to deliver the air to the air inlet from the air outlet of the manifold.

16. The system of claim 15, wherein the air supply is at least one of an air pump and a compressed air canister.

17. A system configured to atomize fluid into an environment, comprising:

a manifold, a plurality of the systems of claim 13, with each system being a cartridge attached to the manifold, and an air supply, connected to the manifold, wherein the manifold is configured to receive the air from the air supply, and the manifold is configured to deliver the air to the air inlet of each of the cartridges.

18. The system of claim 17, wherein the air supply is at least one of an air pump and a compressed air canister.

* * * * *

UNITED STATES PATENT AND TRADEMARK OFFICE

CERTIFICATE OF CORRECTION

PATENT NO. : 12,329,903 B2
APPLICATION NO. : 17/689517
DATED : June 17, 2025
INVENTOR(S) : Michael Kaczkowski It is certified that error appears in the above-identified patent and that said Letters Patent is hereby corrected as shown below:

In the Claims

Column 9, Line 6, please delete "and"

Signed and Sealed this
Nineteenth Day of August, 2025

Coke Morgan Stewart
*Acting Director of the United States Patent and Trademark Office*